US012681011B2

(12) United States Patent
Berry et al.

(10) Patent No.: US 12,681,011 B2
(45) Date of Patent: Jul. 14, 2026

(54) OPTICAL COVID-19 DETECTION SYSTEM

(71) Applicant: THE BOARD OF TRUSTEES OF THE UNIVERSITY OF ILLINOIS, Urbana, IL (US)

(72) Inventors: Vikas Berry, Chicago, IL (US); Ngoc Hoang Lan Nguyen, Hillsboro, OR (US); Sungjoon Kim, Chicago, IL (US)

(73) Assignee: THE BOARD OF TRUSTEES OF THE UNIVERSITY OF ILLINOIS, Urbana, IL (US)

( * ) Notice: Subject to any disclaimer, the term of this patent is extended or adjusted under 35 U.S.C. 154(b) by 1026 days.

(21) Appl. No.: 17/696,749

(22) Filed: Mar. 16, 2022

(65) Prior Publication Data

US 2022/0299506 A1     Sep. 22, 2022

Related U.S. Application Data

(60) Provisional application No. 63/161,879, filed on Mar. 16, 2021.

(51) Int. Cl.
| | |
|---|---|
| *G01N 33/543* | (2006.01) |
| *G01N 33/551* | (2006.01) |
| *G01N 33/569* | (2006.01) |

(52) U.S. Cl.
CPC ..... *G01N 33/54373* (2013.01); *G01N 33/551* (2013.01); *G01N 33/56983* (2013.01);
(Continued)

(58) Field of Classification Search
CPC ........... G01N 33/54373; G01N 33/551; G01N 33/56983; G01N 2333/165;
(Continued)

(56) References Cited

U.S. PATENT DOCUMENTS

| | | | |
|---|---|---|---|
| 2006/0286124 A1* | 12/2006 | Burt ..................... | A61K 39/215 |
| | | | 435/456 |
| 2016/0054312 A1* | 2/2016 | Goldsmith ........... | C12Q 1/6869 |
| | | | 506/39 |

(Continued)

FOREIGN PATENT DOCUMENTS

WO     WO-2019173220 A1 *  9/2019

OTHER PUBLICATIONS

Seo, G. (2020). Rapid Detection of COVID-19 Causative Virus (SARS-CoV-2) in Human Nasopharyngeal Swab Specimens Using Field-Effect Transistor Based Biosensor. ACS Nano. 14, 5135-5142. (Year: 2020).*

(Continued)

*Primary Examiner* — Charles Capozzi
*Assistant Examiner* — Jacqueline Brazin
(74) *Attorney, Agent, or Firm* — GrowIP Law Group LLC

(57)     ABSTRACT

The disclosure provides example devices and methods for making and using the devices for rapid testing for the SARS-CoV-2 virus. The example device includes (a) a substrate coupled to a metal oxide layer, (b) a graphene layer coupled to the metal oxide layer, (c) a chemical or biochemical linker functionalized with the graphene layer, and (d) a plurality of SARS-CoV-2 receptors that are bound to the graphene layer via the chemical or biochemical linker, wherein the plurality of SARS-CoV-2 receptors comprise SARS-CoV-2 spike antibodies or SARS-CoV-2 spike proteins, where the graphene layer is configured to have a first phononic energy, when the plurality of SARS-CoV-2 receptors are unattached to target molecules, and a second phononic energy, when the plurality of SARS-CoV-2 receptors are attached to target molecules.

19 Claims, 6 Drawing Sheets

(52) U.S. Cl.
CPC ... *G01N 2333/165* (2013.01); *G01N 2469/10* (2013.01); *G01N 2469/20* (2013.01)

(58) Field of Classification Search
CPC .......... G01N 2469/10; G01N 2469/20; G01N 21/65; G01N 33/531; G01N 33/553
USPC ...................................................... 435/283.1
See application file for complete search history.

(56) References Cited

U.S. PATENT DOCUMENTS

| | | | | |
|---|---|---|---|---|
| 2017/0316487 | A1* | 11/2017 | Mazed | G06Q 30/0241 |
| 2020/0240949 | A1* | 7/2020 | Atkins | G01N 27/4145 |
| 2022/0074882 | A1* | 3/2022 | Witt | G01N 27/308 |
| 2022/0252584 | A1* | 8/2022 | Ban | G01N 27/4145 |
| 2022/0387995 | A1* | 12/2022 | Kurabayashi | G01N 33/54366 |

OTHER PUBLICATIONS

International Search Report for PCT/US2022/020625 mailed on Jun. 22, 2022 (Entire Document).
Jiang Zixin et al: "Graphene biosensors for bacterial and viral pathogens", Biosensors and Bioelectronics, vol. 166, Jul. 25, 2020 (Jul. 25, 2020), pp. 1-19, XP055928763, Amsterdam , NL ISSN: 0956-5663, DOI: 10.1016/j.bios.2020.112471.
Nguyen Ngoc Hoang Lan et al: "COVID-19 Spike Protein Induced Phononic Modification in Antibody-Coupled Graphene for Viral Detection Application", ACS NANO, vol. 15, No. 7, Jun. 15, 2021 (Jun. 15, 2021), pp. 11743-11752, XP055930204, US ISSN: 1936-0851, DOI: 10.1021/acsnano.lc02549 Retrieved from the Internet: URL: https://vikasb.people.uic.edu/papers/B erry-ACS-Nano-COVID-Graphene.pdf.
Sadighbayan Deniz: "Biosensing based on field-effect transistors (FET): recent progress and challenges", Oct. 9, 2020 (Oct. 9, 2020), pp. 1-16, XP055841997, Retrieved from the Internet: URL:https://www.ncbi.nlm.nih.gov/pmc/artic les/PMC7545218/pdf/main.pdf [retrieved on Sep. 17, 2021].
Seo Giwan et al: "Rapid Detection of COVID-19 Causative Virus ( SARS-CoV-2) in Human Nasopharyngeal Swab Specimens Using Field-Effect Transistor-Based Biosensor", ACS NANO, vol. 14, No. 4, Apr. 15, 2020 (Apr. 15, 2020), pp. 5135-5142, XP055787405, US ISSN: 1936-0851, DOI: 10.1021/acsnano.0c02823 abs; fig 1, "Fabrication of Graphene-Based Sensing Devices"; "Immobilization of SARS-CoV-2 Antibody on the Graphene Surface."
Vermisoglou Eleni et al: "Human virus detection with graphene-based materials", Biosensors and Bioelectronics, Jul. 22, 2020 (Jul. 22, 2020), XP055819395, Retrieved from the Internet: URL:https://www.ncbi.nlm.nih.gov/pmc/artic les/PMC7375321/pdf/main.pdf.

* cited by examiner

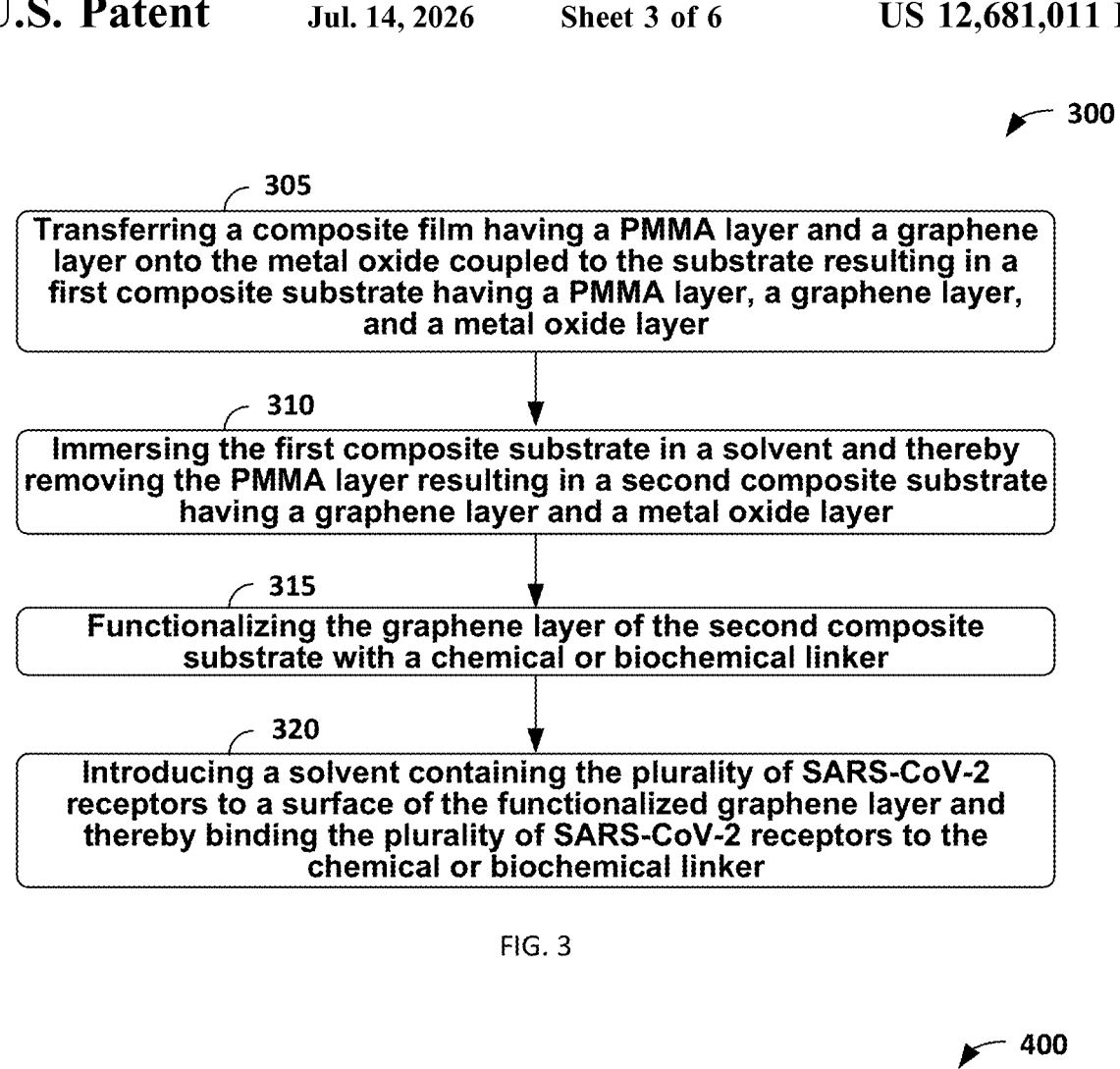

300

305
Transferring a composite film having a PMMA layer and a graphene layer onto the metal oxide coupled to the substrate resulting in a first composite substrate having a PMMA layer, a graphene layer, and a metal oxide layer 310
Immersing the first composite substrate in a solvent and thereby removing the PMMA layer resulting in a second composite substrate having a graphene layer and a metal oxide layer 315
Functionalizing the graphene layer of the second composite substrate with a chemical or biochemical linker 320
Introducing a solvent containing the plurality of SARS-CoV-2 receptors to a surface of the functionalized graphene layer and thereby binding the plurality of SARS-CoV-2 receptors to the chemical or biochemical linker

405
Obtaining, via a Raman spectrometer, the first phononic energy from a target location on the graphene layer of the device to establish a testing baseline 410
Introducing a solution containing a saliva or a nasal sample to a surface of the functionalized graphene layer 415
Obtaining, via the Raman spectrometer, the second phononic energy from the target location of the graphene layer 420
Determining whether a Raman shift between the first phononic energy and the second phononic energy exceeds a threshold value indicative of the presence of the target molecules

FIG. 4

OPTICAL COVID-19 DETECTION SYSTEM

CROSS-REFERENCE TO RELATED APPLICATION

This application claims the benefit of the filing date of U.S. Provisional Patent Application No. 63/161,879, filed on Mar. 16, 2021, which is hereby incorporated by reference in its entirety.

BACKGROUND

With an incubation time of about 5 days, early diagnosis of severe acute respiratory syndrome coronavirus 2 (SARS-CoV-2) is critical to control the spread of the coronavirus disease 2019 (COVID-19) that killed about 1.5 million people in its first year. Due to the rapid infection rate and the lack of vaccine, fast, early and cost-effective detection and diagnosis is very crucial to identify infected individuals.

SUMMARY

The disclosure provides a device, method of manufacture, and rapid testing method to detect either the SARS-CoV-2 spike protein that includes the receptor binding domain or the SARS-CoV-2 spike antibody using Raman spectroscopic analysis of interfaced graphene. A graphene surface of the device is chemically modified with an antibody with specific affinity to components of the spike protein present in samples containing SARS-CoV-2 protein to detect the presence of the SARS-CoV-2 virus. Alternatively, the graphene surface of the device is chemically modified with a spike protein with specific affinity to components of the spike antibody present in samples containing SARS-CoV-2 protein to act as an antigen test. Upon interfacing with the spike protein, graphene undergoes a change in doping density and its phononic energy reflected in Raman spectroscopy. Employing an exemplary system constructed in accordance with the principles herein, Raman spectroscopy could detect SARS-CoV-2 spike protein in phosphate buffered saline solution embedded in the device at low concentrations, such as for detection limits of <1 microg/ml).

Coronavirus disease 2019 (COVID-19) is caused by severe acute respiratory syndrome coronavirus 2 (SARS-CoV-2). Due to the rapid infection rate and the lack of vaccine, fast, early and cost-effective diagnosis is very crucial. Herein a rapid, accurate and affordable COVID-19 detection device and method is set forth with a graphene device that is simple to manufacture.

To this extent, an optical (photonic and phononic) method and system to detect COVID via Graphene Plasmonics is set forth. In comparison to some of the electrical methods: (a) this method does not require intensive lithographic techniques to build the device (cost-effective), (b) it is easier and faster to measure, (c) there are no electrochemical side-reactions (since there is no applied electric field), and (d) the sample preparation is minimal.

In a first aspect, an example device is disclosed. The device includes (a) a substrate coupled to a metal oxide layer, (b) a graphene layer coupled to the metal oxide layer, (c) a chemical or biochemical linker functionalized with the graphene layer, and (d) a plurality of SARS-CoV-2 receptors that are bound to the graphene layer via the chemical or biochemical linker, where the plurality of SARS-CoV-2 receptors comprise SARS-CoV-2 spike antibodies or SARS-CoV-2 spike proteins, where the graphene layer is configured to have a first phononic energy, when the plurality of SARS-CoV-2 receptors are unattached to target molecules, and a second phononic energy, when the plurality of SARS-CoV-2 receptors are attached to target molecules.

In a second aspect, an example method for making the device according to the first aspect is disclosed. The method includes (a) transferring a composite film having a polymethyl methacrylate (PMMA) layer and a graphene layer onto the metal oxide coupled to the substrate resulting in a first composite substrate having a PMMA layer, a graphene layer, and a metal oxide layer, (b) immersing the first composite substrate in a solvent and thereby removing the PMMA layer resulting in a second composite substrate having a graphene layer and a metal oxide layer, (c) functionalizing the graphene layer of the second composite substrate with a chemical or biochemical linker, and (d) introducing a solvent containing the plurality of SARS-CoV-2 receptors to a surface of the functionalized graphene layer and thereby binding the plurality of SARS-CoV-2 receptors to the chemical or biochemical linker.

In a third aspect, an example method for using the device according to the first aspect is disclosed. The method includes (a) obtaining, via a Raman spectrometer, the first phononic energy from a target location on the graphene layer of the device to establish a testing baseline, (b) introducing a solution containing a saliva or a nasal sample to a surface of the functionalized graphene layer, (c) obtaining, via the Raman spectrometer, the second phononic energy from the target location of the graphene layer; and (d) determining whether a Raman shift between the first phononic energy and the second phononic energy exceeds a threshold value indicative of the presence of the target molecules.

The features, functions, and advantages that have been discussed can be achieved independently in various examples or may be combined in yet other examples further details of which can be seen with reference to the following description and drawings.

BRIEF DESCRIPTION OF THE DRAWINGS

FIG. 3 is a flow diagram of a method for making the device, according to one example implementation;

FIG. 4 is a flow diagram of a method for using the device, according to one example implementation;

Figures 1A, 1B:
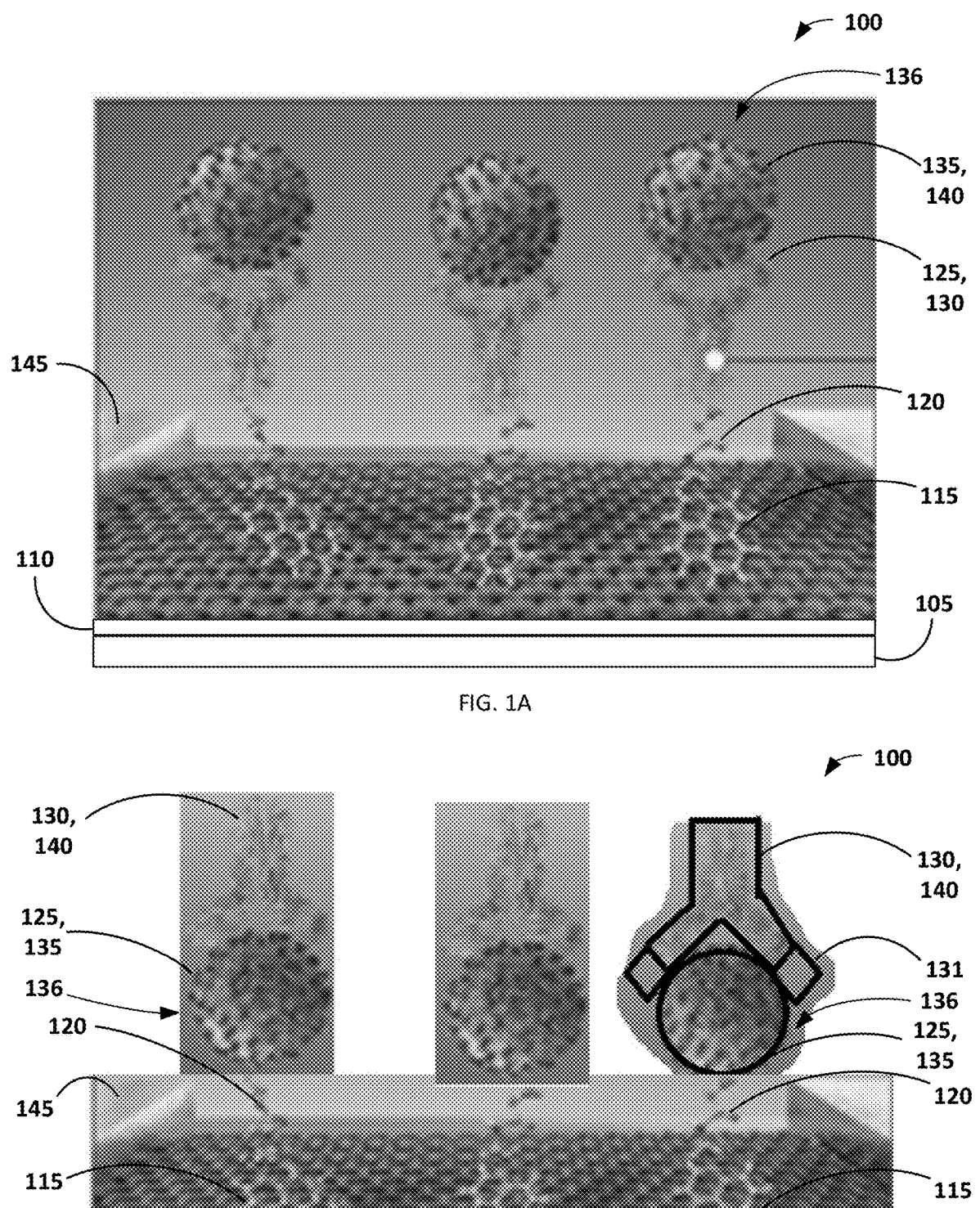
FIG. 1A is a schematic representation of the device having a plurality of SARS-CoV-2 receptors in the form of the SARS-CoV-2 spike antibodies, according to one example implementation.
FIG. 1B is a schematic representation of the device having a plurality of SARS-CoV-2 receptors in the form of the SARS-CoV-2 spike proteins, according to one example implementation.

The drawings are for the purpose of illustrating examples, but it is understood that the inventions are not limited to the arrangements and instrumentalities shown in the drawings

DETAILED DESCRIPTION

The disclosed examples provide a device configured to rapidly detect SARS-CoV-2 spike proteins or SARS-CoV-2 spike antibodies, as well as methods to make and use the device. The device advantageously demonstrates sensitivity to a detection limit of 1 fg/ml of SARS-CoV-2 antigen spike protein. The device also beneficially has selectivity for the type of protein present in a test sample resulting from the precision of antibody-antigen binding.

Figure 2:
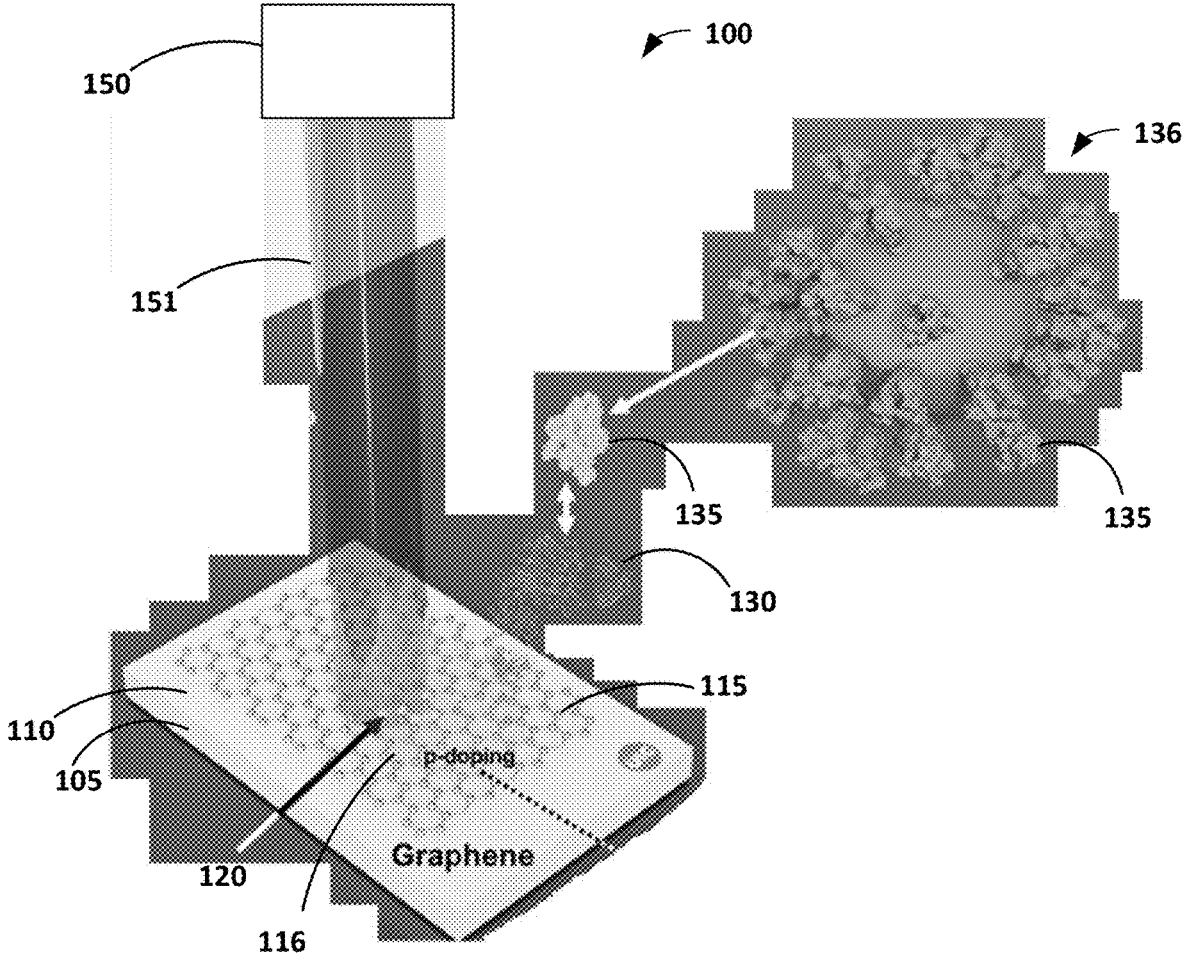
FIG. 2 is a schematic depicting the device in use with a laser deployed during Raman spectroscopy after application to the graphene layer of a solution containing target molecules in the form of SARS-CoV-2 spike proteins, according to one example implementation.

FIGS. 1A-1B depict a device 100 that includes a substrate 105 coupled to a metal oxide layer 110. The device 100 also includes a graphene layer 115 coupled to the metal oxide layer 110. The graphene layer 115 is a monolayer, in particular a single layer of carbon atoms, tightly bound in a hexagonal honeycomb lattice, as shown in FIGS. 1A, 1B, and 2. While FIGS. 1A and 1B show portions of the graphene layer 115 extending away from the substrate 105 of the device 100, this is for illustration purposes only. In operation, the graphene layer 115 is planar.

The substrate 105 provides support for the metal oxide layer 110 and the graphene layer 115 to avoid defects or distortions of the graphene lattice structure. The substrate 105 may include glass or PET, or any other appropriate material known in the art. In some example implementations, the substrate 105 and the metal oxide layer 110 may be formed from the same material, e.g. a metal oxide chip, such that the metal oxide layer 110 has a sufficient thickness to act as the substrate 105.

The device 100 further includes a chemical or biochemical linker 120 that is functionalized with the graphene layer 115. In one optional implementation, the chemical or biochemical linker 120 includes a plurality of metal atoms functionalized with the graphene layer 115 with an eta-6, eta-5, eta-4, eta-3, eta-2, or eta 1 chemistry such that the plurality of metal atoms each bind at a first end 121 to the graphene layer 115 and at a second end 122 with one of the plurality of SARS-CoV-2 spike antibodies 130 or spike proteins 135. In a further implementation, the chemical or biochemical linker 120 is a 1-Pyrenebutyric acid N-hydroxysuccinimide ester (PBASE) linker. The foregoing functionalization techniques advantageously allow retention of the graphene layer's phononic properties (e.g., 2D and G peak positions for phonon vibrational modes) for testing purposes.

The device 100 also includes a plurality of SARS-CoV-2 receptors 125 that are bound to the graphene layer 115 via the chemical or biochemical linker 120. The plurality of SARS-CoV-2 receptors 125 include SARS-CoV-2 spike antibodies 130 or SARS-CoV-2 spike proteins 135. The graphene layer 115 is further configured to have a first phononic energy, when the plurality of SARS-CoV-2 receptors 125 are unattached to target molecules 140, and a second phononic energy, when the plurality of SARS-CoV-2 receptors 125 are attached to target molecules 140.

As shown in one example implementation in FIG. 1A, the plurality of SARS-CoV-2 receptors 125 are SARS-CoV-2 spike antibodies 130 and the attached target molecules 140 are SARS-CoV-2 spike proteins 135. In this arrangement, the device 100 is configured to detect the presence of the SARS-CoV-2 virus 136. In an alternative example implementation shown in FIG. 1B, the plurality of SARS-CoV-2 receptors 125 are SARS-CoV-2 spike proteins 135 and the attached target molecules 140 are SARS-CoV-2 spike antibodies 130. In this arrangement, the device 100 is configured as an antigen test for active infection. As shown in FIG. 1B, the target molecules 140 include both SARS-CoV-2 spike antibodies 130, as well as antigens 131 that may be bound to those antibodies 130.

In an optional example implementation, the metal oxide layer 110 includes indium tin oxide ("ITO") or Si/SiO$_2$, or any other metal oxide that provides appropriate n-doping properties to the graphene, when the target molecules 140 are unattached to the SARS-CoV-2 receptors 125. In a further optional implementation, the metal oxide layer 110 is indium tin oxide. In this example, the substrate 105 and the metal oxide layer 110 may optionally be in the form of a unitary ITO chip. In this example, the graphene layer 115 is n-doped, when the plurality of SARS-CoV-2 receptors 125 are unattached to the target molecules 140. This is because ITO is inherently n-doped. In a further implementation, the graphene layer 115 is configured to be p-doped, when the plurality of SARS-CoV-2 receptors 125 are attached to the target molecules 140. As a result, the graphene layer 115 has a first phononic energy and corresponding 2D peak position, when the graphene layer is n-doped, and a second phononic energy and corresponding 2D peak position that increases once the graphene layer 115 becomes p-doped. The effect of the change in the phononic energy and 2D peak position is discussed in more detail with respect to method 400 and the example section discussed below.

Alternatively, using Si/SiO$_2$ as the metal oxide layer 110 will initially result in a graphene layer 115 that has both n-doped and p-doped regions prior to exposure to the solution containing the test sample. As a result, a target location 116 will need to be identified that has sufficient n-doping, where the initial 2D peak position is lower relative to other regions on the graphene layer 115. This target location 116 will then be used for both readings of the 2D peak position before and after exposure to the solution containing a sample for testing. In the ITO example, any region on the graphene layer 115 may be used as the target location 116 to obtain the 2D peak positions before and after exposure to the testing sample.

In one optional implementation, as shown in FIGS. 1A-2, the device 100 includes a housing 145 coupled to the substrate 105. The housing 145 is configured to be repeatably-received by a Raman spectrometer 150 to align a laser 151 with a target location 116 on the graphene layer 115 and to determine the first phononic energy from the target location 116 and the second phononic energy from the target location 116. The housing 145 may include directional indicators to facilitate loading and reloading of the device 100 into the Raman spectrometer 150 in the same orientation to obtain pre-exposure and post-exposure data from the same target location 116. In an optional implementation, the Raman spectrometer 150 is handheld for deployment at a rapid testing facility, such as a pharmacy. In one example, the laser focal size may be on the order of 700 nm and used with the device 100 having a square shape and dimensions of 0.5 μm×0.5 μm. If a given Raman spectrometer's focal size is larger than 700 nm, then the overall size or footprint of the device 100 would also need to increase.

In one optional implementation, the plurality of SARS-CoV-2 spike antibodies include a first-type of SARS-CoV-2 spike antibodies having an affinity for a first-type of SARS-CoV-2 spike protein for a first-type of SARS-CoV-2 variant and a second-type of SARS-CoV-2 spike antibodies having an affinity for a second-type of SARS-CoV-2 spike protein for a second-type of SARS-CoV-2 variant. This example would permit multiple Covid variants, such as SARS-CoV-2 and MERS-CoV, to be tested on the same device 100 for a given sample.

The following methods 300 and 400 may include one or more operations, functions, or actions as illustrated by one or more of blocks 305-320 and 405-420. Although the blocks are illustrated in a sequential order, these blocks may also be performed in parallel, and/or in a different order than those described herein. Also, the various blocks may be combined into fewer blocks, divided into additional blocks, and/or removed based upon the desired implementation. Alternative implementations are included within the scope of the examples of the present disclosure in which functions may be executed out of order from that shown or discussed, including substantially concurrent or in reverse order, depending on the functionality involved, as would be understood by those reasonably skilled in the art.

Referring now to FIG. 3, FIG. 3 shows a flowchart of an example method 300 for making the device 100, according to an example implementation. Method 300 includes, at block 305, transferring a composite film having a PMMA layer and a graphene layer onto the metal oxide coupled to the substrate resulting in a first composite substrate having a PMMA layer, a graphene layer, and a metal oxide layer. Then, at block 310, the first composite substrate is immersed in a solvent and thereby removes the PMMA layer resulting in a second composite substrate having a graphene layer and a metal oxide layer. Next, at block 315, the graphene layer of the second composite substrate is functionalized with a chemical or biochemical linker. And, at block 320, a solvent containing the plurality of SARS-CoV-2 receptors is introduced to a surface of the functionalized graphene layer and thereby binds the plurality of SARS-CoV-2 receptors to the chemical or biochemical linker.

In one optional implementation, functionalizing the graphene layer of the second composite substrate with a chemical or biochemical linker includes functionalizing the graphene layer of the second composite substrate with an eta-6, eta-5, eta-4, eta-3, eta-2, or eta 1 chemistry such that a plurality of metal atoms each bind at a first end to the graphene layer and have a second end configured to bind with one of the plurality of SARS-CoV-2 receptors.

In one optional implementation, method 400 further includes, prior to transferring the composite film having the PMMA layer and the graphene layer onto the metal oxide coupled to the substrate, growing the graphene layer on a metal foil using a low-pressure chemical vapor deposition. Next, a PMMA solution is spin-coated onto the graphene layer on the metal foil, thereby resulting in a three-layered composite foil. And then, the three-layered composite foil is etched in a solvent until the metal foil dissolves thereby resulting in the composite film.

In various implementations, the graphene can be grown on any suitable metal foil, such as Copper, Nickle, Cobalt, or Cobalt oxide. In one optional implementation, growing the graphene layer on the metal foil includes heating the metal foil to a temperature above 900° C. in a chamber with a carbon containing gas for at least two minutes and at a pressure less than 10 mTorr. Then, the metal foil is further oxidized using CVD with air or oxygen at temperature less than 500° C. Oxidizing the metal foil is important, since high p-doping of graphene can reduce the sensitivity of the device 100.

In another optional implementation, the method 300 includes, after immersing the first composite substrate in a solvent, annealing the second composite substrate to reduce contaminants. This annealing may be conducted at a high temperature and at a low pressure.

Referring now to FIG. 4, FIG. 4 shows a flowchart of an example method 400 for using the device 100, according to an example implementation. Method 400, includes at block 405, obtaining, via a Raman spectrometer, the first phononic energy from a target location 116 on the graphene layer 115 of the device 100 to establish a testing baseline. Then, at block 410, a solution containing a saliva or a nasal sample is introduced to a surface of the functionalized graphene layer 115. Next, at block 415, the Raman spectrometer obtains the second phononic energy from the target location 116 of the graphene layer 115. And, at block 420, the method 400 includes determining whether a Raman shift between the first phononic energy and the second phononic energy exceeds a threshold value indicative of the presence of the target molecules 140. In one example implementation, the first phononic energy and the second phononic energy each correspond to a Raman 2D peak position.

In one example implementation, the threshold value is 0.8 $cm^{-1}$ for the phononic shift. Detection of the virus in accordance with the principles herein was found to be accurate for a concentration of 1 pg/ml for the SARS-CoV-2 spike protein.

In another example implementation, the method 400 includes, after introducing the solution containing the saliva or the nasal sample to the surface of the functionalized graphene layer, washing the device 100 and thereby removing non-specifically bound molecules in the solution from the device 100. For example, if the target molecule was the SARS-CoV-2 spike protein and the sample included MERS-CoV, then the MERS-CoV spike protein would not bind to the SARS-CoV-2 spike antibodies and would wash away to avoid disrupting the post-exposure 2D peak position measurement.

In another example implementation, washing the device 100 includes washing the device with a phosphate-buffered saline solvent. For example, the device 100 may be placed in a beaker for 30 seconds with the solvent. Then, the device 100 is washed with a PBS solvent. This may be accomplished by holding the device 100 vertically under a running flow of the phosphate buffered saline (PBS) solvent five times using a pipet. And next, the device 100 is washed with deionized water. The device 100 may again be arranging vertically and washed under a flow of deionized water five times using a pipet. In a further implementation, after washing the device 100, the device 100 is dried with nitrogen gas flow.

EXAMPLE

Introduction

In December 2019, a highly infectious coronavirus disease 2019 (COVID-19) was first reported in Wuhan, China. In March 2020, the World Health Organization (WHO) classified the COVID-19 as a pandemic; which by December 2020 had taken 1.5 million lives and infected more than 55 million people. The COVID-19 virus belongs to beta-coronavirus family with SARS-CoV (severe acute respiratory syndrome coronavirus) and MERS-CoV (Middle East respiratory syndrome coronavirus). COVID-19 is caused by the SARS-CoV-2, which is composed of a single stranded RNA genome enclosed in a membrane forming a spherical structure approximately 125 nm in diameter. There are four major proteins encoded by the COVID-19 genome: the spike (S) protein, nucleocapsid (N) protein, membrane (M) protein and the envelope (E) protein. Structurally, the spike protein is composed of a transmembrane anchor, a short intracellular tail, and a large ectodomain, which includes the receptor binding domain. Functionally, the spike protein is responsible for binding with the host cell receptors (such as angiotensin converting enzyme 2 (ACE-2)), which mediates the entry of the virus into the target cells. Due to its functional importance and its location on the outer shell of the COVID-19, this work is focused on the effect of the interfacing of the spike (S) protein on the phononics of graphene.

Since a large population of people that contract the virus are asymptomatic and most others develop symptoms in 3 to 5 days (due to the long viral incubation time), fast diagnosis is critical in controlling the pandemic. The most-widely used method to detect COVID-19 is real time reverse transcription polymerase chain reaction (RT-PCR). The single-strand RNA from viruses in a sample is extracted and transcribed into a complementary DNA. This DNA is then amplified for several cycles via PCR for fluorescence detection. However, this method requires the RNA preparation and translation steps which are time-consuming, labor intensive, and can still affect diagnostic accuracy. In addition, PCR requires several reagents, and the transportation to facility can increase turnaround times to days. This necessitates the development of a virus detection platform which is simple, capable of providing quick results while still being reliable.

In this work, we show the change in phononics of antibody-coupled-graphene with the selective-interfacing of COVID-19 spike protein for its detection (FIG. 2). Among the available phononic modes (D, D', G, 2D and 2D'), graphene's properties are predominantly represented by 3 phonon vibrational modes: D-band peak (intervalley phonon) near 1350 cm$^{-1}$, G-band peak ($E_{2g}$, primary in-plane vibrational mode) around 1580 cm$^{-1}$, and 2D-band peak (second order overtone of a different in-plane vibrational mode) at about 2670 cm$^{-1}$ (peak positions are for 532 nm incident laser). Since graphene has a monoatomic thickness, these peaks are highly sensitive to graphene's structural, electronic, and interfacial properties. In particular, Raman peak positions correlate strongly with graphene's doping level represented by the concentration of injected carriers in graphene (dopants/cm$^2$).

While the 2D peak position increases with p-doping and decreases with n-doping (for both n- and p-type), the G peak position increases with n-doping for n-type graphene and with p-doping in p-type graphene. This implies that the G band can only provide information on the change in carrier density, while the 2D band can provide the carrier density and the polarity of doping. In addition, G band (Raman-active E2g Γ phonon mode) has Kohn anomaly behavior. By heavy doping, the adiabatic Born-Oppenheimer approximation, which is valid in many solid state system breaks down, causing phononic vibration for the G peak to stiffen and eventually result in saturation of the G peak shift. However, since the nonadiabatic effect does not influence the 2D phonon, 2D band position is not limited by high carrier concentration. Therefore, antibody-coupled-graphene's 2D peak position is studied and used to calculate the doping concentration and polarity for the identification of the COVID-19 spike protein. This work includes specific binding agents on graphene for improved selectivity. This detection platform can be employed for whole viral particle detection and this is a direct measurement of a viral antigen attachment, unlike indirect methods, where the diagnosis is based on the translated molecules.

Any molecule coming in close proximity to graphene can modify graphene's carrier concentration via two prominent mechanisms: (a) charge transfer due to the relative positions of the Fermi level of graphene and the HOMO (for electron donors) or LUMO (for electron acceptors) levels of the interfacing molecule, and (b) dipole moment gating, which is amplified by the large quantum capacitance of graphene. This doping modifies the 2D phonon's resonance condition (FIG. 2), which renormalizes the electronic band. When the electronic band is pushed away from the Dirac point, the absolute value of electron energy increases, leading to the decrease in the lifetime of the excited quasiparticles and phonon momentum. This process causes a change in the 2D mode Raman shift and its scattering phononic energies correspondingly. It is important to note that high quality graphene is critical for this process because defects (lattice disorders and oxy-groups) lead to the combination of inter-valley phonon and defect scattering forming the D peak; thus, significantly suppressing the two phonon scattering of the 2D peak. Moreover, the defect sites on graphene lattice can attract non-specific bindings, which would affect the selectivity of the biosensors.

As a sensing platform, the elegant mechanism of graphene chemeo-phononics lends simplicity to the final device construct: (a) No electrical connections are required eliminating the need for expensive and time-consuming photo- or electron-lithographic techniques; (b) Direct and fast measurements; (c) No electrochemical side-reactions; and (d) Requires fewer reagents. The main challenge of the technique is the relative high cost of the Raman spectrometer required for detection and the data analysis.

In this work, graphene is functionalized with a CoV-2 spike RBD antibody (amino acids sequence from Arg 319 to Phe 541; 40592-T62; Sino Biological, Inc., China) that binds specifically to the CoV-2 spike RBD protein (amino acids sequence from Arg 319 to Phe 541; ab27065; Abcam, Inc., USA). The vicinity of the spike protein bound to the antibody leads to a p-doping of the p-type graphene; in turn, causing a blue shift in the 2D peak. This graphene phononic device was sensitive to the detection limit of 1 pg/ml of SARS-CoV-2 antigen spike protein. Moreover, the sensor showed selectivity due to the precision of antibody-antigen binding. It could distinguish SARS-CoV-2 spike protein from its previous member in betacorona virus family: MERS-CoV spike protein.

Result and Discussion

Figure 5A:
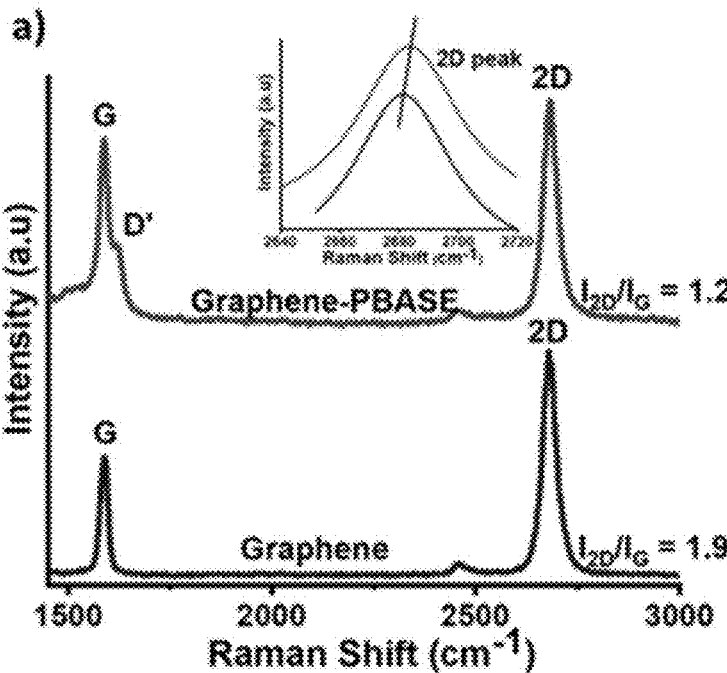
FIG. 5A shows representative Raman spectra of the pristine graphene and 1-pyrenebutyric acid N-hydroxysuccinimide ester (PBASE)-treated graphene. The inset shows an upshift of Raman 2D band after attachment of PBASE.

The detection was carried out on graphene sheet produced via chemical vapor deposition (CVD) on copper foil and transferred on Si/SiO$_2$ 300 nm wafer. Due to the oxy- and hydroxyl-groups on silicon oxide surface, the graphene-on-SiO$_2$ becomes a p-type semimetal. To immobilize the antibody on graphene, graphene is first interfaced with 1-Pyrenebutyric acid N-hydroxysuccinimide ester (PBASE) linker, which has an aromatic pyrene group that binds with graphene via π-π interaction and an amine-reactive group that binds with the amino acid groups in the specific antibody of SARS-CoV-2 Spike protein (FIG. 2). The PBASE reaction is carried out in methanol for 1 hour at room temperature. It is known that based on the HOMO and LUMO of the aromatic molecules and the electron-withdrawing or electron-donating groups, they can either p-dope or n-dope graphenic materials, respectively. The ester and nitrogen groups in PBASE are responsible for withdrawing the electrons directly from graphene to p-dope it; and the work function of graphene increases by 0.5 eV after PBASE attachment, indicating electrons transfer from graphene's Fermi level to the LUMO level of PBASE. Here, the electronic band is pushed further below the Dirac point, which is reflected in a blue-shift of 2D peak position (FIG. 5A, discussed next). In addition, the van der Waals force between the graphene and the pyrene backbone of PBASE molecule ensures their tight binding and retention of the sp$^2$-carbon lattice construct.

The functionalization of graphene with the linker PBASE is an important step, because it allows the immobilization of the spike antibody as a receptor biomolecule on graphene, which will bind specifically to COVID-19 spike protein (target biomolecule). To confirm the attachment of PBASE on graphene, Raman spectroscopy and X-ray photoelectron spectroscopy data were collected. All Raman spectra were acquired using a confocal Raman microscope (Raman-AFM, WITec alpha 300 RA, laser wavelength of 532 nm). The laser spot size was 721 nm with a 50× objective lens (ZEISS). FIG. 5A shows a comparison between Raman spectra of pristine graphene and graphene functionalized with PBASE. In pristine graphene, the presence of two major G and 2D peaks with very small D peak indicates the pristine quality of the transferred graphene with minimal defects (high intensity ratio I$_{2D}$/I$_G$=1.9 and I$_D$/I$_G$=0.4). After the reaction with PBASE, there was an emergence of the D' (1623 cm$^{-1}$) peaks. The D' peak is attributed to a resonance of pyrene group onto the graphene surface and the high edge-density. This confirms the attachment of PBASE onto the graphene. In addition, 2D peak position was shifted to a higher frequency and the I$_{2D}$/I$_G$ ratio decreases after the attachment.

Figure 5B:
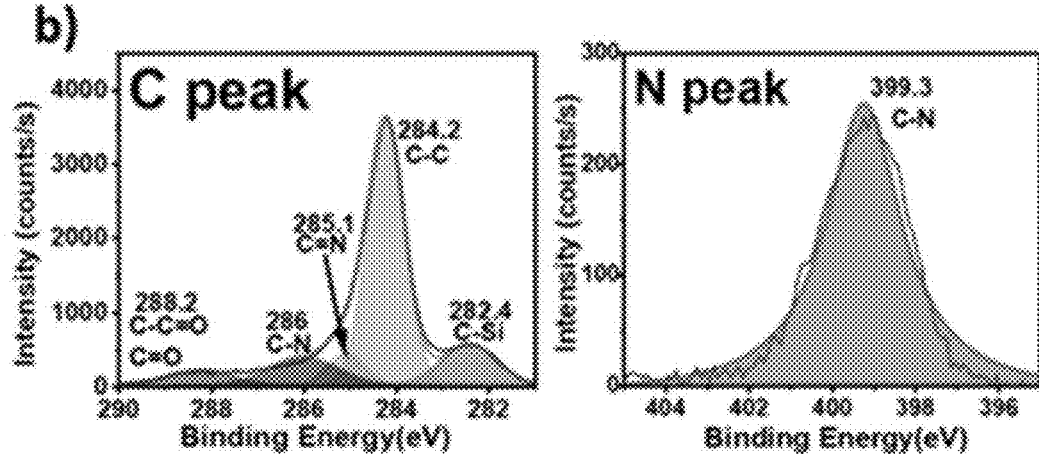
FIG. 5B shows high-resolution XPS spectra of graphene-PBASE at C 1s peak and N 1s peak, respectively.

FIG. 5B shows the high-resolution X-ray photoelectron spectroscopy (XPS, Kratos AXIS-165) spectra of PBASE-treated graphene at C 1s peak and N 1s peak. The appearance of the core N 1s peak further confirms the presence of PBASE on graphene. In particular, the peak at a binding energy (B.E.) of ~399 eV is assigned to the C—N bonds. The C 1s peak was deconvoluted into four components: 282.4; 284.2; 286; 288.2 eV corresponding to C—Si, C=N, C—N, and C=O/C—C=O bonds, respectively. While the strongest peak (C=C) is attributed to graphene, the presence of oxygen functionalized carbon C=O/C—C=O is due to the residue of poly(methyl methacrylate) (PMMA) from the graphene transferring process. More importantly, the presence of C—N peak in both C 1s peak and N 1s peak scans confirm the chemical attachment of PBASE on graphene.

Figure 5C:
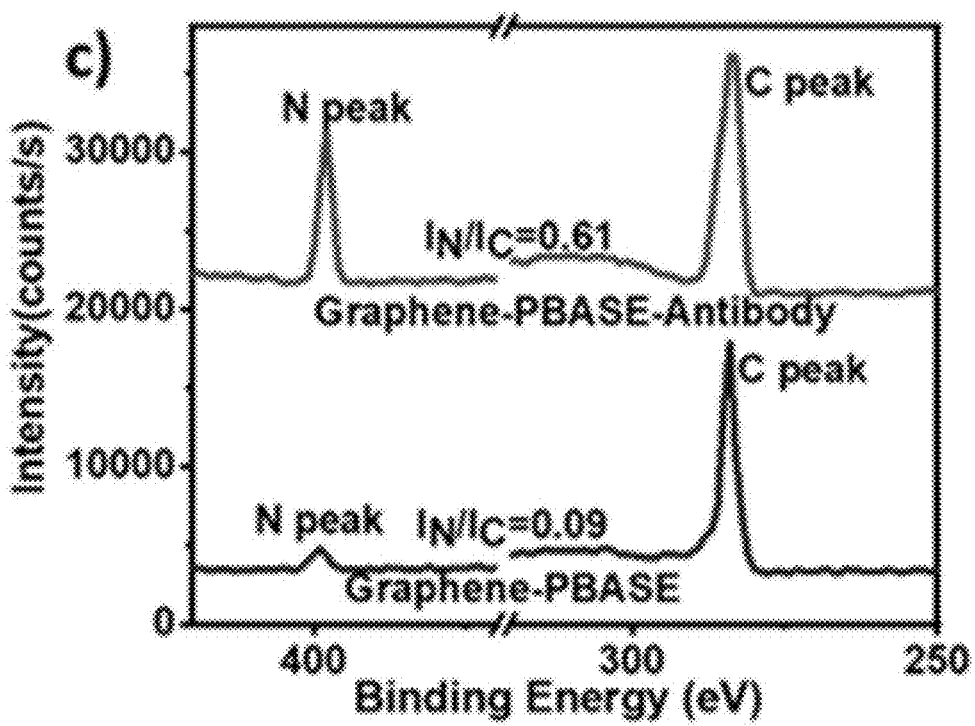
FIG. 5C shows XPS survey scans of graphene-PBASE and graphene-PBASE-Antibody structures, according to an example implementation.

The immobilization of SARS-CoV-2 spike antibody on PBASE-modified graphene was performed through the interaction between antibody amine (—NH$_2$) group and N-hydroxysuccinimide ester group of PBASE. The XPS survey data from FIG. 5C reveals that after antibody modification, there is a significant increase in the intensity of N 1s peak. Although there is a slight increase in C 1 s peak intensity, the ratio between N 1s:C 1s peak intensities increased 6.6 times (0.09 to 0.61) after antibody attachment. This increase in the number of nitrogen atoms is attributed to the amino acid groups of the antibody. In addition, from the analysis of the XPS peaks of C and N, the ratio of the nitrogen and the carbon atoms added is 0.275, consistent with the composition of a typical protein, confirming the attachment of the antibody.

Figure 6:
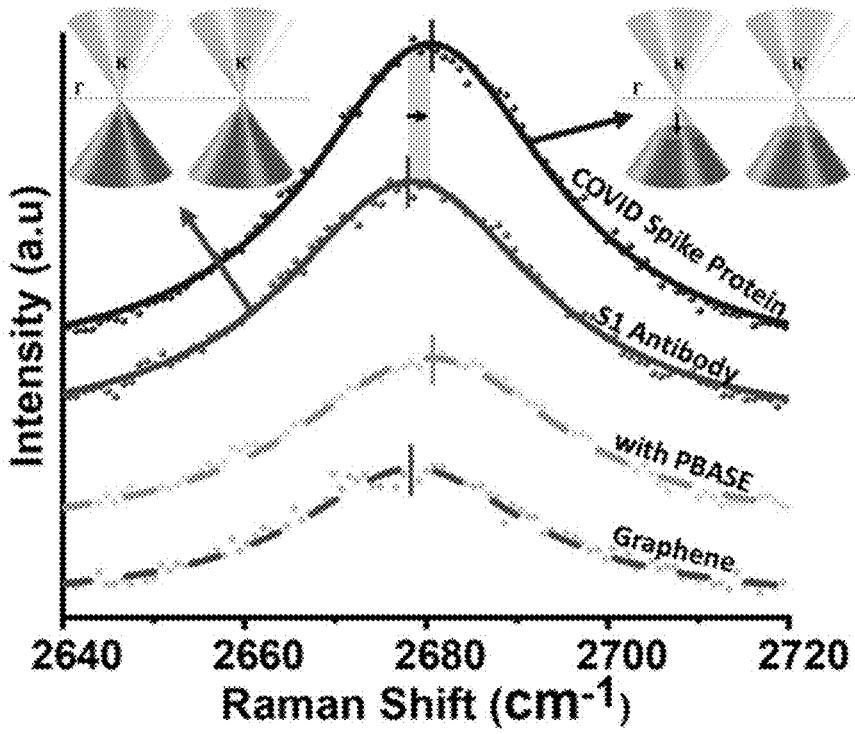
FIG. 6 shows SARS-CoV-2 spike protein detection via graphene phononics, including the 2D peak of graphene, PBASE-modified graphene, graphene-PBASE-antibody, and graphene-PBASE-antibody-spike protein. As shown, the attachment of PBASE p-dopes the device, the antibody n-dopes the device, and the COVID protein attachment p-dopes the device by $2.07 \pm 0.168$ cm$^{-1}$.

To investigate the performance of the graphene phononic sensor, we interfaced SARS-CoV-2 spike protein on the graphene-PBASE-antibody structure and acquired the Raman data. It is important to note that 2D band peak position are different on different areas and different samples; and is affected by the substrate interactions, defects, and surface roughness. Therefore, the Raman scans were acquired at the exact same area for each of the process-steps: graphene, PBASE-modified graphene, graphene-PBASE-antibody, and graphene-PBASE-antibody-spike protein structure. Here, a representative data scan collected to compare the doping effect after each reaction is shown in FIG. 6. Initially, graphene's 2D band peak position (green) was at 2678.61 cm$^{-1}$. This higher value is attributed to the p-doping from SiO$_2$ substrate (work function (5.0 eV) less than that of graphene, as discussed earlier). The 2D peak full-width at half maxima (FWHM) of the initial p-doped graphene is 31.1 cm$^{-1}$, which indicates that the graphene is single layer (i.e., good quality).

On the same area, PBASE π-stacking attachment showed a blue shift of 1.89 cm$^{-1}$ (from 2678.61 cm$^{-1}$ to 2680.5 cm$^{-1}$). As mentioned earlier, this p-doping effect is attributed to the nitrogen and ester groups on the PBASE that withdraw electrons from graphene. Next, the attachment of the spike antibody exhibited n-doping (electron injection) with the 2D peak position red-shift of 2.11 cm$^{-1}$ (from 2680.5 cm$^{-1}$ to 2678.39 cm$^{-1}$). This can be explained by the replacement of N-Hydroxysuccinimide (NHS) group in PBASE with the amine group in the antibody. Because the NHS ester, which consists of two N—C=O centers, is an electron withdrawing group, the removal of NHS group makes graphene less p-doped, which is represented by a decrease of the 2D band peak wavenumber.

Finally, upon the attachment of the spike protein, there was a p-doping of graphene with a blue-shift in 2D peak position of 2.07 cm$^{-1}$, from 2678.39 cm$^{-1}$ to 2680.46 cm$^{-1}$. Studies have shown that the HOMO of S1 Spike protein is −5.16 eV which is lower than Fermi level of modified graphene: −4.7 eV. This means that electrons will not transfer directly due to the energy level difference between the protein and graphene. Similarly, the LUMO of S1 Spike protein at −2.77 eV is higher than Fermi level of modified graphene, indicating that electrons will not be withdrawn from graphene to the protein. Thus, the p-doping effect of the protein is the result of induced charge carriers. When the spike protein coming in close proximity to the graphene sheet, the molecular dipoles on the protein apply an electric field (or a small gating voltage) on graphene. The polarity of the induced charge carriers is opposite to the polarity of the applied voltage. As the protein has a negative potential, positive charge carriers were doped, leading to a p-doping effect.

Graphene ultrasensitive doping is an outcome of high quantum capacitance $C_Q$. For monolayer graphene, $$C_Q = \frac{4e^2 \sqrt{\pi}}{h v_F} \sqrt{n_T},$$

where h is the Planck's constant, $v_f \approx c/300$ is the Fermi velocity of the Dirac electron, e is the electron charge, and $n_T$ is the total charge concentration of graphene. As graphene has a large quantum capacitance, a small potential (V) from any dipole moment can lead to high change in electric charge (Q) on graphene (or doping effect). Further, the 2D peak position can be correlated with the change in the Fermi level and the p-doping for p-type graphene by these following equations: 2D pos.$=-2 \times 10^{-10} \times E_f^4 - 6 \times 10^{-8} \times E_f^3 + 6 \times 10^{-5} \times E_f^2 - 0.0003 \times E_f + 2676.7$, p-density$=0.6 \times 10^7 \times (E_f)^2$, and the induced potential doping is estimated by $$\Delta V = \frac{\Delta Q}{C_Q}.$$

With this, it is estimated: the change in Fermi level $\Delta E_f = -82.7$ meV; the change in p-doping density $\Delta p = 4.1 \times 10^{11}$ dopant/cm$^2$; and induced voltage $V-12.8$ mV for spike protein attachment. In addition, the FWHM of graphene-PBASE-antibody-protein structure is 32.9 cm$^{-1}$ (1.8 cm$^{-1}$ increase from initial graphene), showing that the graphene quality (low defect density) was maintained during all three steps.

Figure 7A:
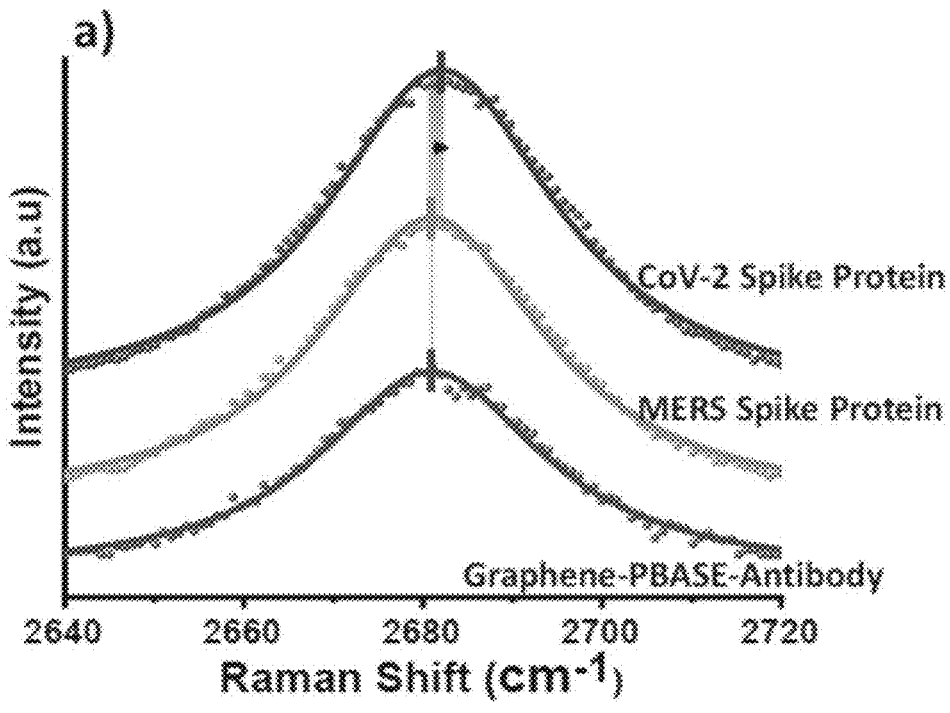
FIG. 7A shows the 2D Raman peak spectra of graphene-PBASE-antibody device, after interaction with MERS-CoV protein, and after interaction with the SARS-CoV-2 spike protein structure. While the interaction with the MERS-CoV protein did not change the peak position, the interaction with the SARS-CoV-2 spike protein changed the 2D peak position by 1.18 cm$^{-1} \pm 0.2$ cm$^{-1}$, thereby demonstrating selectivity and sensitivity of the device.
Figure 7B:
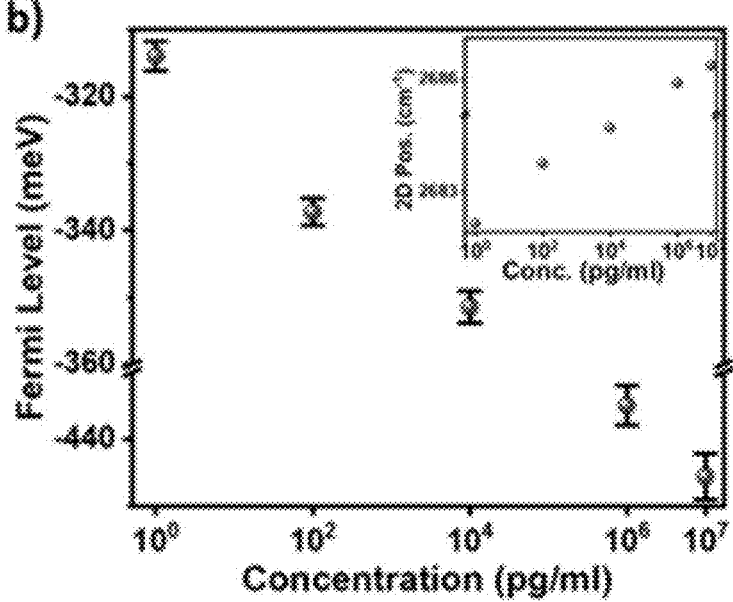
FIG. 7B shows the 2D peak position (inset) and the Fermi level of graphene changes with the concentration of the SARS-CoV-2 spike protein (at 1 pg/ml, 100 pg/ml, 10 ng/ml, 1 ug/ml and 10 ug/ml). This graph shows that the device can detect a concentration at 1 pg/ml with a peak shift of 0.83 cm$^{-1}$ and a Fermi level change of $-26.9$ meV.

To investigate the selectivity of the phononic device, the antibody-coupled-graphene was interfaced with MERS-CoV spike protein as a control. As before, the exact same area of graphene was scanned for each of the steps in this experiment. Similar to other tests, PBASE interaction showed p-doping, while the SARS-CoV-2 spike antibody attachment showed n-doping. The graphene-PBASE-antibody structure (shown in FIG. 7A) was exposed to MERS-CoV spike protein 10 ug/ml to check the selectivity of the device. The Raman 2D peak shows practically no shift (0.06 cm$^{-1}$ increase within the error range of $\pm 24$ cm$^{-1}$), which indicates no change in graphene's energy band. This result can be directly attributed to the lack of interaction between the SARS-CoV-2 antibody and the MERS-CoV spike protein. The same device was then interfaced with the SARS-CoV-2 protein and a p-doping was observed as expected (shown in FIG. 7A). The 2D band peak position upshifts 1.18 cm$^{-1}$ from 2680.91 cm$^{-1}$ (the antibody) to 2682.09 cm$^{-1}$ (SARS-CoV-2 spike protein). From the 2D peak position, the change in the Fermi and doping levels are estimated: $\Delta E_f = -38.9$ meV; $\Delta p = 9.1 \times 10^{10}$ dopant/cm$^2$. These observations confirm that the antibody is specific for the SARS-CoV-2 spike protein and is therefore suitable for detecting SARS-CoV-2. More experiments are required for testing other proteins, their mixtures and for statistical analysis of false positives and negatives.

To measure the sensor's sensitivity and limit of detection for spike protein, experiments were conducted at five different concentrations of the spike protein: 1 pg/ml, 100 pg/ml, 10 ng/ml, 1 ug/ml, and 10 ug/ml. On one graphene-PBASE-antibody area, the five different concentrations were exposed with increasing concentrations. The results show an increase in the Raman shift with the higher spike protein concentration. With the lowest concentration of 1 pg/ml (approximately $1.5 \times 10^7$ molecules/ml), there was a 0.83 cm$^{-1}$ blue-shift. This Raman shift (from the antibody) increased to 1.55 cm$^{-1}$, 1.98 cm$^{-1}$, 4.17 cm$^{-1}$ and 4.38 cm$^{-1}$ with 100 pg/ml, 10 ng/ml, 1 ug/ml and 10 ug/ml, respectively. Correspondingly, the Fermi level decreases from $-313.9$ meV at 1 pg/ml to $-337.3$, $-351.5$, $-434.9$, and $-445.6$ meV at 100 pg/ml, 10 ng/ml, 1 ug/ml and 10 ug/ml respectively. The decreasing Fermi level of graphene with higher concentration of CoV-2 S-protein reflects an increase of p-doping due to an increase in protein attachment. The saturating behavior for Fermi level change at higher spike protein concentration is attributed to the decreasing number of unoccupied surface antibody sites on the surface. A summary of the change in Fermi level and doping effect of different SARS-CoV-2 Spike protein concentrations are reflected in the table below.

| Concentration | 2D peak position | $\Delta E_f$ (meV) | $\Delta p \left( 10^{11} \frac{dopant}{cm^2} \right)$ |
|---|---|---|---|
| Antibody | 2681.79 | | |
| 1 pg/ml | 2682.62 | $-26.9$ | 9.7 |
| 100 pg/ml | 2683.34 | $-23.4$ | 9.1 |
| 10 ng/ml | 2683.77 | $-14.2$ | 5.7 |
| 1 ug/ml | 2685.96 | $-83.5$ | 39.4 |
| 10 ug/ml | 2686.17 | $-10.6$ | 5.6 |

Conclusion

The high infection rate, long incubation period, and the possibility of asymptomatic infection necessitates the need for the development of rapid and sensitive detection techniques. In this work, the sensitive and selective phononic response of antibody-coupled-graphene to CoV-2-spike protein as a foundation for COVID-19 phononic sensor. The sensor showed no measurable cross-reactivity with MERS-CoV spike protein and was able to detect SARS-CoV-2 spike protein at 1 pg/ml level. The graphene phononic sensor is a competitive platform compared to other detection methods due to its unique advantages which include facile fabrication, real-time response, and selective detection of target molecules. The versatility of the chemeo-phononic system, the surface chemistry can be modified to diagnose other diseases which are conventionally difficult to monitor.

Materials and Methods

Graphene growth: Graphene was grown on 25-μm thick copper foil (Alfa Aesar, 99.8%) using low-pressure chemical vapour deposition (LPCVD). Copper foils were immersed in $Fe(NO_3)_3$:$HNO_3$ solution (1 mol $Fe(NO_3)_3$ and 3 mol $HNO_3$) solution for 10 minutes for pre-treatment to clean copper oxide and impurities. After taken out from $Fe(NO_3)_3$:$HNO_3$ solution, copper foil was washed by acetone, IPA and blow-dried with Na gas. This clean Cu foil was then placed in a CVD furnace quartz tube and the tube was allowed to reach a vacuum of <10 mTorr to reduce any further contamination in the system. After reaching low pressure, CVD system was heated to 1050° C. from room temperature 25° C. under 10 SCCM $H_2$ in 25 minutes. At 1050° C., the copper foil was annealed for a further 40 minutes with 10 SCCM $H_2$ to prepare the copper foil surface for the deposition. The actual deposition occurs in the presence of precursor $CH_4$ at 10 SCCM with $H_2$ flow rate of 50 SCCM. After 10 minutes of reaction, $CH_4$ flow rate was removed to stop the supply of carbon source. $H_2$ flow was retained during the cool down step of the process.

Transfer graphene: $Si/SiO_2$ 300 nm wafer chip was treated with Piranha solution for 1 hour and washed by DI water, acetone, isopropyl alcohol (IPA), air blow before the transfer. Graphene was transferred onto $Si/SiO_2$ 300 nm using poly methyl methacrylate (PMMA). PMMA powder is dissolved in anisole solvent at concentration of 25 mg/mL. Then the PMMA solution is spin-coated onto graphene on copper foil at 500 RPM in 5 seconds ramping 500 RPM/s, followed by 4000 RPM in 30 seconds ramping 1000 RPM/s. After that the PMMA/graphene/copper foil was etched in $HNO_3$ 98%:$H_2O$ (1:3 by volume) for 1 hour until all the copper is dissolved. The PMMA-graphene composite film that floated on the top was transferred to at least two DI water baths to remove the acid residues. Then the PMMA/graphene layer is then transferred onto a $Si/SiO_2$ chip and dried overnight. After that, PMMA layer is removed by immersing the chip in acetone for 15 minutes. Then, the chip is washed by acetone, IPA and dried with air blow. Finally, the chip is annealed at high temperature and low pressure to further reduce polymer and other sources of contamination.

Functionalize graphene with PBASE: PBASE powder is stored in freezer (−5 to −30° C.) and protected from light. Graphene on $Si/SiO_2$ wafer was immersed in 2 mM of PBASE in methanol for 1 hour at room temperature. Afterwards, the PBASE modified graphene was washed with methanol and dried with $N_2$.

Immobilize SARS-CoV-2 spike antibody on graphene surface: 10 μl of SARS-CoV-2 spike antibody of 250 ug/mL in PBS (pH=7.4) solvent was dropped on graphene-PBASE. The immobilization reaction lasted for 4 hours at 4° C. The chip was then rinsed with PBS, DI water, and dried with $N_2$.

Immobilize SARS-CoV-2 spike protein and MERS-CoV protein on graphene surface: SARS-CoV-2 and MERS-CoV spike proteins in PBS (pH=7.4) solvent at different concentrations was dropped on the graphene-PBASE-antibody structure. The reactions lasted for 30 minutes at 4° C. After that, the chip was rinsed with PBS, DI water and dried with $N_2$.

The invention claimed is:

1. A device, comprising:
a substrate coupled to a metal oxide layer;
a graphene layer coupled to the metal oxide layer;
a chemical or biochemical linker functionalized with the graphene layer;
a plurality of SARS-COV-2 receptors that are bound to the graphene layer via the chemical or biochemical linker, wherein the plurality of SARS-COV-2 receptors comprise SARS-COV-2 spike antibodies or SARS-COV-2 spike proteins, wherein binding of target molecules to the plurality of SARS-COV-2 receptors changes a phononic energy of the graphene layer from a first phononic energy to a second phononic energy; and
a housing coupled to the substrate, wherein the housing provides unobstructed optical access to a target location on the graphene layer for Raman spectroscopy measurements, and wherein the housing comprises alignment features that enable repeatable positioning of the device relative to a Raman spectrometer for alignment of a laser with the target location on the graphene layer, wherein the optical access permits determination of the first phononic energy from the target location and the second phononic energy from the target location via Raman spectroscopy.

2. The device of claim 1, wherein the metal oxide layer comprises indium tin oxide ("ITO") or $Si/SiO_2$.

3. The device of claim 1, wherein the metal oxide layer is indium tin oxide, wherein the graphene layer is n-doped, when the plurality of SARS-COV-2 receptors are unattached to the target molecules.

4. The device of claim 3, wherein the graphene layer is configured to be p-doped, when the plurality of SARS-COV-2 receptors are attached to the target molecules.

5. The device of claim 1, wherein the chemical or biochemical linker comprises a plurality of metal atoms functionalized with the graphene layer with an eta-6, eta-5, eta-4, eta-3, eta-2, or eta 1 chemistry such that the plurality of metal atoms each bind at a first end to the graphene layer and at a second end with one of the plurality of SARS-COV-2 spike antibodies or spike proteins.

6. The device of claim 1, wherein the chemical or biochemical linker is a 1-Pyrenebutyric acid N-hydroxysuccinimide ester (PBASE) linker.

7. The device of claim 1, wherein the graphene layer is a monolayer.

8. The device of claim 1, wherein the plurality of SARS-COV-2 spike antibodies comprises a first-type of SARS-COV-2 spike antibodies having an affinity for a first-type of SARS-COV-2 spike protein for a first-type of SARS-COV-2 variant and a second-type of SARS-CoV-2 spike antibodies having an affinity for a second-type of SARS-COV-2 spike protein for a second-type of SARS-COV-2 variant.

9. A method for making the device of claim 1, the method comprising:
transferring a composite film having a PMMA layer and a graphene layer onto the metal oxide coupled to the substrate resulting in a first composite substrate having a PMMA layer, a graphene layer, and a metal oxide layer;
immersing the first composite substrate in a solvent and thereby removing the PMMA layer resulting in a second composite substrate having a graphene layer and a metal oxide layer;
functionalizing the graphene layer of the second composite substrate with a chemical or biochemical linker; and
introducing a solvent containing the plurality of SARS-COV-2 receptors to a surface of the functionalized graphene layer and thereby binding the plurality of SARS-COV-2 receptors to the chemical or biochemical linker.

10. The method of claim 9, wherein functionalizing the graphene layer of the second composite substrate with a chemical or biochemical linker comprises functionalizing the graphene layer of the second composite substrate with an eta-6, eta-5, eta-4, eta-3, eta-2, or eta 1 chemistry such that a plurality of metal atoms each bind at a first end to the graphene layer and have a second end configured to bind with one of the plurality of SARS-COV-2 receptors.

11. The method of claim 9, further comprising:
prior to transferring the composite film having the PMMA layer and the graphene layer onto the metal oxide coupled to the substrate, growing the graphene layer on a metal foil using a low-pressure chemical vapor deposition;
spin-coating a PMMA solution onto the graphene layer on the metal foil, thereby resulting in a three-layered composite foil; and
etching the three-layered composite foil in a solvent until the metal foil dissolves thereby resulting in the composite film.

12. The method of claim 9, wherein growing the graphene layer on the metal foil comprises:

heating the metal foil to temperature above 900° C. in a chamber with a carbon containing gas for at least two minutes and at a pressure less than 10 mTorr; and further oxidizing the metal foil using CVD with air or oxygen at temperature less than 500° C.

13. The method of claim 9, further comprising:

after immersing the first composite substrate in a solvent, annealing the second composite substrate to reduce contaminants.

14. A method for using the device of claim 1, the method comprising:

obtaining, via the Raman spectrometer, the first phononic energy from the target location on the graphene layer of the device to establish a testing baseline;

introducing a solution containing a saliva or a nasal sample to a surface of the functionalized graphene layer;

obtaining, via the Raman spectrometer, the second phononic energy from the target location of the graphene layer; and determining whether a Raman shift between the first phononic energy and the second phononic energy exceeds a threshold value indicative of the presence of the target molecules.

15. The method of claim 14, wherein the threshold value is 0.8 cm$^{-1}$.

16. The method of claim 14, further comprising:

after introducing the solution containing the saliva or the nasal sample to the surface of the functionalized graphene layer, washing the device and thereby removing non-specifically bound molecules in the solution from the device.

17. The method of claim 16, wherein washing the device comprises:

washing the device with a phosphate-buffered saline solvent;

washing the device with a PBS solvent; and washing the device with deionized water.

18. The method of claim 17, further comprising:

after washing the device, drying the device with nitrogen gas flow.

19. The method of claim 14, wherein the first phononic energy and the second phononic energy each correspond to a Raman 2D peak position.

\* \* \* \* \*